United States Patent
Shelly et al.

(10) Patent No.: US 11,672,942 B2
(45) Date of Patent: Jun. 13, 2023

(54) SYSTEM AND METHOD FOR PROVIDING MANDIBULAR ADVANCEMENT AND SLEEP POSITIONAL THERAPY

(71) Applicant: KONINKLIJKE PHILIPS N.V., Eindhoven (NL)

(72) Inventors: Benjamin Irwin Shelly, Pittsburgh, PA (US); Monica H Bush, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 551 days.

(21) Appl. No.: 16/719,208

(22) Filed: Dec. 18, 2019

(65) Prior Publication Data
US 2020/0197655 A1    Jun. 25, 2020

Related U.S. Application Data

(60) Provisional application No. 62/782,414, filed on Dec. 20, 2018.

(51) Int. Cl.
*A61M 21/00* (2006.01)
*A61B 5/08* (2006.01)
(Continued)

(52) U.S. Cl.
CPC .......... *A61M 21/00* (2013.01); *A61B 5/0816* (2013.01); *A61B 5/1116* (2013.01); *A61B 5/486* (2013.01);
(Continued)

(58) Field of Classification Search
CPC .......... A61M 21/00; A61M 2021/0022; A61M 2021/0027; A61M 2021/0044;
(Continued)

(56) References Cited

U.S. PATENT DOCUMENTS 6,935,335 B1* 8/2005 Lehrman ........... A61M 16/0069
600/587
2005/0236003 A1* 10/2005 Meader ................... A61F 5/566
128/848
(Continued)

FOREIGN PATENT DOCUMENTS

| WO | 2011082349 A1 | 12/2010 |
| WO | 2012129397 A1 | 9/2012 |
| WO | 2019185671 A1 | 10/2019 |

OTHER PUBLICATIONS

"The Sleep Position Trainer", NightBalance, Accessed Dec. 16, 2019, https://www.nightbalance.com/spt/.
(Continued)

*Primary Examiner* — Sunita Reddy (57) ABSTRACT

The present disclosure pertains to a system and method for providing mandibular advancement and sleep positional therapy to a user for a sleep session. The system is formed by a mandibular advancement device for treating obstructive sleep disordered breathing (e.g., obstructive sleep apnea and snoring) that includes an electronics module configured to aid in sleep positional training. The present system and method facilitate advancing a lower jaw of the user into a protruding position relative to an upper jaw of the user to increase a size of an airway of the user, determining whether a posture of the user has breached a posture threshold, and, responsive to a breach, prompting the user to change posture such that the posture of the user no longer breaches the posture threshold.

11 Claims, 3 Drawing Sheets

(51) Int. Cl.
    *A61B 5/11*     (2006.01)
    *A61B 5/00*     (2006.01)
    *A61F 5/56*     (2006.01)

(52) U.S. Cl.
    CPC .......... *A61B 5/4812* (2013.01); *A61B 5/4818* (2013.01); *A61B 5/4848* (2013.01); *A61F 5/566* (2013.01); *A61B 2562/0204* (2013.01); *A61B 2562/0219* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2205/05* (2013.01); *A61M 2205/3303* (2013.01); *A61M 2205/3375* (2013.01); *A61M 2205/50* (2013.01); *A61M 2205/52* (2013.01); *A61M 2230/42* (2013.01); *A61M 2230/62* (2013.01)

(58) Field of Classification Search
    CPC .. A61M 2021/0055; A61M 2021/0072; A61M 2205/05; A61M 2205/3303; A61M 2205/3375; A61M 2205/50; A61M 2205/52; A61M 2230/42; A61M 2230/62; A61B 5/0816; A61B 5/1116; A61B 5/4812; A61B 5/4818; A61B 5/4848; A61B 5/486; A61B 2562/0204; A61B 2562/0219; A61B 5/11; A61B 5/4542; A61B 5/4561; A61B 5/4806; A61B 5/682; A61F 5/566
    USPC .................................................. 128/846, 848
    See application file for complete search history.

(56) References Cited

U.S. PATENT DOCUMENTS

| | | | | |
|---|---|---|---|---|
| 2008/0289637 | A1* | 11/2008 | Wyss .................... | A61F 5/566 128/848 |
| 2011/0180076 | A1* | 7/2011 | Hegde .................... | A61F 5/566 128/848 |
| 2011/0295083 | A1* | 12/2011 | Doelling ................ | A61B 5/11 600/407 |
| 2013/0043999 | A1 | 2/2013 | Van Beest | |
| 2013/0118504 | A1* | 5/2013 | Hermanson ....... | A61M 16/0488 128/848 |
| 2014/0135868 | A1* | 5/2014 | Bashyam ............ | A61N 1/3601 607/42 |
| 2014/0180036 | A1* | 6/2014 | Bukkapatnam ...... | A61B 5/0816 128/845 |
| 2016/0199215 | A1* | 7/2016 | Kopelman ............. | A61F 5/566 128/848 |
| 2016/0324681 | A1 | 11/2016 | Flanagan | |
| 2017/0087360 | A1* | 3/2017 | Scheiner ............... | A61B 5/1116 |
| 2017/0196727 | A1 | 7/2017 | Giridharagopalan | |
| 2019/0358449 | A1* | 11/2019 | Kent .................... | A61B 5/0826 |

OTHER PUBLICATIONS

International Search Report and Written Opinion, International Application No. PCT/EP2019/085211, dated Mar. 10, 2020.

* cited by examiner

FIG. 3

SYSTEM AND METHOD FOR PROVIDING MANDIBULAR ADVANCEMENT AND SLEEP POSITIONAL THERAPY

CROSS-REFERENCE TO PRIOR APPLICATIONS

This application claims the benefit of U.S. Provisional Application No. 62/782,414, filed on 20 Dec. 2019. This application is hereby incorporated by reference herein.

BACKGROUND

1. Field

The present disclosure pertains to a system and method for providing mandibular advancement and sleep positional therapy to a user for a sleep session.

2. Description of the Related Art

Electronic positional sleep therapy devices are known. One such device is described in US Patent Application Publication Number 2013/0043999. Typical positional sleep therapy devices detect whether a user is sleeping on his or her back and provide vibratory feedback to the user that prompts the user to change his or her position. A more traditional method of positional sleep training is known as the "Tennis Ball Technique". With this technique, a tennis ball is sewn into the back of a shirt worn to bed by the user so that the user finds sleeping on his or her back uncomfortable. Mandibular advancement devices are also known. Known electronic positional sleep therapy devices, the Tennis Ball Technique, and mandibular advancement devices do not provide any other sleep assistance to a user beyond the individual operations each separate device or technique is configured to perform.

SUMMARY

It would be advantageous to provide a single system that provided both mandibular advancement and sleep positional therapy to a user for a sleep session.

Accordingly, one or more aspects of the present disclosure relate to a system configured to provide mandibular advancement and sleep positional therapy to a user for a sleep session. The system comprises a mandibular advancement mouthpiece, one or more posture sensors, one or more sensory stimulators, a controller, and/or other components. The mandibular advancement mouthpiece is configured to: removably couple with teeth of the user; and advance a lower jaw of the user into a protruding position relative to an upper jaw of the user to increase a size of an airway of the user. The one or more posture sensors are configured to generate output signals conveying information related to a posture of the user. The one or more sensory stimulators are configured to provide sensory stimulation to the user. The controller is electronically coupled to the one or more posture sensors and the one or more sensory stimulators. The controller is configured to determine, based on the output signals, whether the posture of the user has breached a posture threshold, and, responsive to a breach, cause the one or more sensory stimulators to provide first sensory stimulation to the user to prompt the user to change posture such that the posture of the user no longer breaches the posture threshold. The controller, the one or more sensory stimulators, and the one or more posture sensors are physically coupled to the mandibular advancement mouthpiece.

In some embodiments, the physical coupling between the controller, the one or more sensory stimulators, the one or more posture sensors, and the mandibular advancement mouthpiece is releasable. In some embodiments, the controller, the one or more sensory stimulators, and the one or more posture sensors are physically coupled to the mandibular advancement mouthpiece (1) via a housing that protrudes from the mandibular advancement mouthpiece outside a mouth of the user, (2) along an interior lower jaw surface of the mandibular advancement mouthpiece; and/or (3) between upper and lower jaw portions of the mandibular advancement mouthpiece.

In some embodiments, the one or more posture sensors comprise an accelerometer and/or other sensors.

In some embodiments, the one or more posture sensors are further configured to generate output signals conveying information related to respiration of the user, and the controller is further configured to determine whether the user experiences a sleep disordered breathing event based on the information related to respiration of the user. In some embodiments, the controller is further configured to cause the one or more sensory stimulators to deliver the sensory stimulation responsive to: a determination that the posture of the user breached the posture threshold, and a determination that the user experienced a sleep disordered breathing event.

In some embodiments, the one or more posture sensors are further configured to generate output signals conveying information related to respiration of the user, the controller is further configured to determine a sleep stage of the user based on the information related to respiration of the user; and the controller is further configured to cause the one or more sensory stimulators to provide the sensory stimulation to the user responsive to the user experiencing an arousal, and/or being in a wakeful or light stage of sleep.

In some embodiments, the system further comprises one or more physiological sensors configured to generate output signals conveying information related to respiration of the user. In some embodiments, the controller is configured to determine whether the user experiences a sleep disordered breathing event and/or a sleep stage of the user based on the information in the output signals from the one or more physiological sensors. In some embodiments, the controller is further configured to cause delivery of the sensory stimulation based on the determination of whether the user experienced a sleep disordered breathing event and/or the sleep stage. In some embodiments, the one or more physiological sensors comprise a microphone and/or other sensors.

In some embodiments, the mandibular advancement mouthpiece is configured such that an amount the lower jaw of the user advances into the protruding position can be adjustable or fixed.

In some embodiments, the system further comprises an electronic application executed by a computing device associated with the user. The electronic application is in communication with the controller, the one or more posture sensors, and/or the one or more sensory stimulators. The electronic application is configured to facilitate review of information related to sleep of the user, respiration of the user, and/or other information. The information related to sleep of the user and/or respiration of the user comprises information related to: a quantity, frequency, timing, and/or type of sleep disordered breathing events in the user; a sleep stage of the user; an effectiveness of the mandibular advancement mouthpiece; a recommended mandibular advancement mouthpiece adjustment; the sensory stimulation provided to the user; and/or other information. In some embodiments, the controller is further configured to determine the information related to the sleep of the user, and/or the respiration of the user.

Another aspect of the present disclosure relates to a method for providing mandibular advancement and sleep positional therapy to a user for a sleep session with a therapy system. The system comprises the mandibular advancement mouthpiece, the one or more posture sensors, the one or more sensory stimulators, the controller, and/or other components. The method comprises facilitating physically coupling the controller, the one or more sensory stimulators, and the one or more posture sensors to the mandibular advancement mouthpiece. The method comprises facilitating, with the mandibular advancement mouthpiece, removable coupling of the mandibular advancement mouthpiece with teeth of the user. The method comprises advancing, with the mandibular advancement mouthpiece, a lower jaw of the user into a protruding position relative to an upper jaw of the user to increase a size of an airway of the user. The method comprises generating, with the one or more posture sensors, output signals conveying information related to a posture of the user. The method comprises determining, with the controller based on the output signals, whether the posture of the user has breached a posture threshold; and responsive to a breach, causing, with the controller, the one or more sensory stimulators to provide first sensory stimulation to the user to prompt the user to change posture such that the posture of the user no longer breaches the posture threshold.

Another aspect of the present disclosure relates to a kit for providing mandibular advancement and sleep positional therapy to a user for a sleep session. The kit comprises the mandibular advancement mouthpiece. The mandibular advancement mouthpiece is configured to: removably couple with teeth of the user; and
advance a lower jaw of the user into a protruding position relative to an upper jaw of the user to increase a size of an airway of the user. The kit comprises the one or more posture sensors configured to generate output signals conveying information related to a posture of the user. The kit comprises the one or more sensory stimulators configured to provide sensory stimulation to the user. The kit comprises the controller configured to determine, based on the output signals, whether the posture of the user has breached a posture threshold, and, responsive to a breach, cause the one or more sensory stimulators to provide first sensory stimulation to the user to prompt the user to change posture such that the posture of the user no longer breaches the posture threshold.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
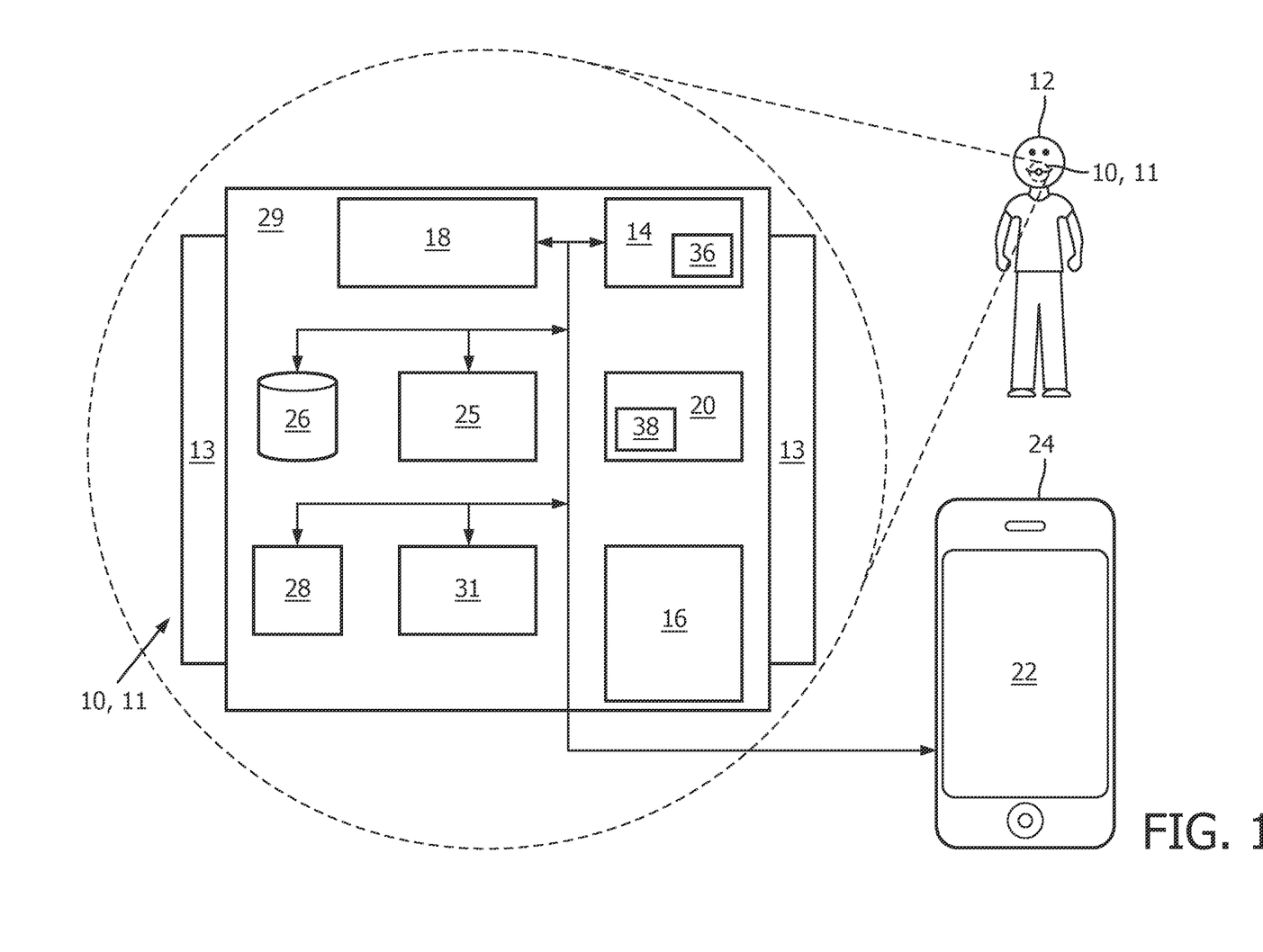
FIG. 1 is a schematic illustration of a system configured to provide mandibular advancement and sleep positional therapy to a user for a sleep session, in accordance with one or more embodiments.

FIG. 1 is a schematic illustration of a system 10 configured to provide mandibular advancement and sleep positional therapy to a user 12 for a sleep session. In some embodiments, a sleep session may comprise any period of time when user 12 is sleeping and/or attempting to sleep. Sleep sessions may include nights of sleep, naps, and/or other sleeps sessions. Positional therapy (or sleep positional training) is an intervention for treating positional obstructive sleep apnea, positional snoring, and/or other conditions in individuals. For some individuals, positional therapy is needed because the individuals fail to adhere to prescribed continuous positive airway pressure (CPAP) therapy regimes, and/or for other reasons. Individuals who suffer from positional obstructive sleep apnea (OSA) or positional snoring are more likely to suffer from anterior-posterior collapse of the soft palate region, from epiglottic closure, or from tongue base closure of the upper airway while lying in a supine position while sleeping, for example. Typically, for these individuals, airway collapse and subsequent sleep disordered breathing events (e.g., snoring, hypopneas, apneas, etc.) occur while sleeping in the supine position, and thus a therapy that encourages sleeping in any non-supine position (e.g., lateral or prone) may resolve the positional OSA and/or snoring.

Often, individuals who suffer from positional OSA or positional snoring do not adhere to prior developed therapies in the long-term. Electronic sleep position training devices that have been developed to help improve adherence provide a stimulus to notify a user to move to a non-supine sleeping position. Mandibular advancement devices are an intervention for treating obstructive sleep disordered breathing that is caused by upper airway structural limitation (i.e., a small airway caused by excess tissue in the upper airway that narrows and may close during sleep). A mandibular advancement device increases upper airway size by advancing the lower jaw into a more protruding position (i.e., making the user have less overjet or retrognathia). Mandibular advancement devices may also be used as an aid to reduce snoring for users who suffer from primary snoring, in the same manner as OSA, for example.

Electronic sleep positional trainers and mandibular advancement devices may be preferable to many users over a continuous positive airway pressure (CPAP) device and should theoretically have higher adherence rates. However, only approximately 50% of patients effectively respond to a mandibular advancement device, and approximately 50% of patients effectively respond to sleep positional therapy. There are no accepted means for predicting which users will effectively respond to a mandibular advancement device. Predicting success of a sleep positional therapy device depends on a diagnostic study (e.g., either in-lab or a home sleep test), which is undesirable for a consumer, and results in non-participation. In addition, any degree of jaw advancement for a mandibular advancement device increases discomfort and the risk of side effects (e.g., temporomandibular joint dysfunction (TMJ)) in a user.

Among other advantages, system 10 provides both mandibular advancement and sleep positional therapy in a single system. System 10 is configured to be effective whether user 12 responds to mandibular advancement, sleep positional therapy, or both. System 10 is configured to remind user 12 to sleep in a lateral (or other non-supine) position. This may decrease the degree of advancement of the lower jaw that needs to be provided by a mandibular advancement device (decreasing and/or avoiding issues with titration), thus increasing comfort, and decreasing the probability of adverse side effects for user 12.

In some embodiments, system 10 includes one or more of a mandibular advancement mouthpiece 13, a posture sensor 14, a physiological sensor 20, a sensory stimulator 16, a controller 18, an electronic application 22, a computing device 24, a user interface 25, electronic storage 26, a power supply 28, communications components 31, a housing 29, and/or other components. In some embodiments, controller 18, sensory stimulator 16, posture sensor 14, physiological sensor 20, and/or other components of system 10 are physically coupled to mandibular advancement mouthpiece 13. In some embodiments, these and/or other components are self-contained (e.g., in housing 29) and physically coupled to mandibular advancement mouthpiece 13 in an unobtrusive manner (e.g., as described herein). In some embodiments, the physical coupling between controller 18, sensory stimulator 16, posture sensors 14, physiological sensor 20, mandibular advancement mouthpiece 13, and/or other components of system 10 is releasable. In some embodiments, system 10 may be configured as a kit 11 of the components described herein such that user 12 may assemble and/or disassemble some or all of system 10.

Mandibular advancement mouthpiece 13 is configured to removably couple with teeth of user 12. Mandibular advancement mouthpiece 13 is configured to advance a lower jaw of user 12 into a protruding position relative to an upper jaw of user 12 to increase a size of an airway of user 12. In some embodiments, mandibular advancement mouthpiece 13 is configured such that an amount the lower jaw of user 12 advances into the protruding position is adjustable or fixed.

Figure 2:
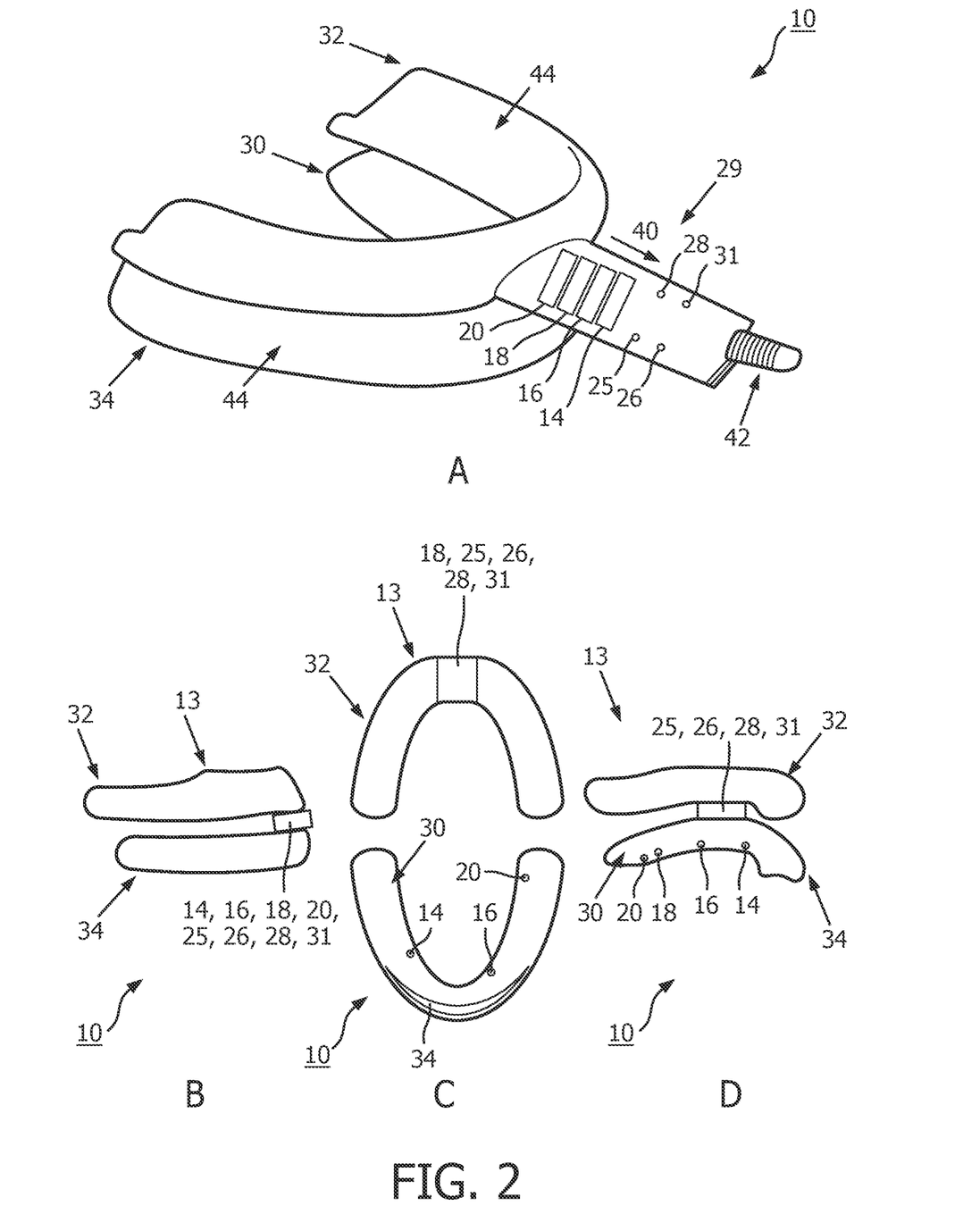
FIG. 2 illustrates views A, B, C, and D of a mandibular advancement mouthpiece and other components of the system, in accordance with one or more embodiments.

FIG. 2 illustrates mandibular advancement mouthpiece 13. FIG. 2 also illustrates various components of system 10 coupled to mandibular advancement mouthpiece 13 in different possible configurations. FIG. 2 includes views A, B, C, and D of various possible embodiments of mandibular advancement mouthpiece 13 and other components of system 10. As shown in view A of FIG. 2, in some embodiments, controller 18, sensory stimulator 16, posture sensor 14, physiological sensor 20, and/or other components of system 10 are physically coupled to mandibular advancement mouthpiece 13 via housing 29 that protrudes 40 from mandibular advancement mouthpiece 13 outside a mouth of the user (not shown in view A). View A also illustrates a threaded adjustment mechanism 42 configured to adjust an amount the lower jaw portion 34 of mandibular advancement mouthpiece 13 (and thus the lower jaw of user 12) advances into the protruding position. In some embodiments, as shown in view A, mandibular advancement mouthpiece 13 is configured to facilitate removable coupling with teeth of the user via a shape and/or form factor 44 of mandibular advancement mouthpiece 13. Mandibular advancement mouthpiece 13 may have a shape and/or form factor 44 configured to engage a corresponding shape and/or form factor of the teeth of the user.

As shown in views B, C, and/or D of FIG. 2, in some embodiments, controller 18, sensory stimulator 16, posture sensor 14, physiological sensor 20, and/or other components of system 10 may be physically coupled to mandibular advancement mouthpiece 13 along an interior lower jaw surface 30 of mandibular advancement mouthpiece 13, between upper 32 and lower 34 jaw portions of mandibular advancement mouthpiece 13, and/or in other locations. Upper jaw portion 32 of mandibular advancement mouthpiece 13 may have a shape and/or form factor that corresponds to an upper jaw and/or teeth of user 12. Lower jaw portion 34 of mandibular advancement mouthpiece 13 may have a shape and/or form factor that corresponds to a lower jaw and/or teeth of user 12. Upper jaw portion 32 and lower jaw portion 34 may be moveably coupled to each other, for example. The locations of the components of system 10 between or along upper 32 and/or lower 34 jaw portions may be relatively unobtrusive for user 12 compared to other locations for these and/or other components of system 10. Unobtrusive may refer to avoiding either obstructing the airway or significantly limiting tongue space. For example, the slimmer the components and closer they are to the back of the teeth or the roof of the mouth, the less likely that a user will be troubled by them as they are attempting to sleep. In some embodiments, housing 29, controller 18, sensory stimulator 16, posture sensor 14, physiological sensor 20, and/or other components of system 10 may be physically coupled to mandibular advancement mouthpiece 13 at the locations described in views A-D and/or other locations via various coupling mechanisms including adhesive, screws, clamps, clips, nuts, bolts, overmolding, and/or other coupling mechanisms.

Returning to FIG. 1, posture sensor 14 is configured to generate output signals conveying information related to a posture of user 12. The output signals are generated during a sleep session of user 12 and/or at other times. Posture may be, or be related to, an overall body position of user 12, a position of one or more body parts of user 12 (e.g., the head and/or neck of user 12), and/or other body position information. Posture sensor 14 may be and/or include an accelerometer 36, a gyroscope, and/or other sensors. Posture sensor 14 is configured to generate output signals that convey information related to an acceleration, and orientation, an angular velocity, movement, and/or other characteristics of user 12. Posture sensor 14 may generate output signals that convey information used to determine whether user 12 is in a supine or a non-supine position, whether user 12 is moving or has moved, whether user 12 (or the head and/or neck of user 12) is in a position that may cause sleep disordered breathing events, and/or other information, for example.

Physiological sensor 20 is configured to generate output signals conveying information related to respiration and/or other physiological characteristics of user 12. For example, physiological sensor 20 is configured to generate output signals conveying information related to breathing parameters such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, airflow rate and/or other parameters, presence of snoring, and/or other breathing parameters of user 12. Physiological sensor 20 may comprise one or more sensors that measure such parameters directly (e.g., by sensing airflow in the mouth of user 12, chest movements of user 12, etc.). Physiological sensor 20 may comprise one or more sensors that generate surrogate output signals related to the one or more breathing parameters indirectly. For example, physiological sensor 20 may comprise one or more sensors configured to generate an output based on sounds made by user 12 (e.g., physiological sensor may be or include a microphone 38), and/or other sensors. In some embodiments, physiological sensor 20 may be and/or include microphone 38, an oral fluid sensor, a thermistor, a pressure sensor (e.g., to measure airflow), and/or other sensors.

In some embodiments, the information in the output signals from posture sensor 14 and/or physiological sensor 20 may be used to determine information related to posture of user 12, respiration of user 12, sleep of user 12, and/or other characteristics of user 12. For example, information in output signals from a breathing rate sensor (e.g., a physiological sensor 20) may be used to determine a respiration pattern, a sleep stage, and/or other information about user 12. As another example, a posture sensor 14 such as an accelerometer may be used to determine the body position of user 12, respiration pattern of user 12 based on movements of user 12 detected by the accelerometer, and/or the sleep stage of user 12 based on movement (or lack thereof) of user 12 during a sleep session (e.g., actigraphy).

As described above, in some embodiments, the information in the output signals from posture sensor 14 and/or physiological sensor 20 may indicate and/or be used to determine information about the sleep of user 12. For example, the information in the output signals from posture sensor 14 and/or physiological sensor 20 may be used to determine whether user 12 is asleep, the sleep stage of user 12, whether user 12 experiences arousals or microarousals, and/or other information. In some embodiments, the sleep stages of user 12 may be wakefulness, REM sleep, NREM Stage 1, 2, or 3 (e.g., N1, N2, N3), and/or other sleep stages.

In some embodiments, the information in the output signals from sensor 14 and/or 20 is used to control sensory stimulator 16 to provide sensory stimulation to user 12 (as described herein). Although sensors 14 and 20 are illustrated in FIG. 1 at a single location in system 10, this is not intended to be limiting. Sensors 14 and 20 may comprise sensors disposed in a plurality of locations, such as for example, at various locations coupled to mandibular advancement mouthpiece 13, within housing 29, and/or at other locations. One or more sensors 14 and/or 20 in these various locations may be in wired and/or wireless communication with controller 18 and/or other components of system 10, for example.

Sensory stimulator 16 is configured to provide sensory stimulation to user 12. Sensory stimulator 16 is configured to provide vibratory, auditory, visual, somatosensory, electric, magnetic, and/or other sensory stimulation to user 12 prior to a sleep session, during a sleep session, and/or at other times. For example, sensory stimulator 16 may be configured to provide stimuli to user 12 during a sleep session to provide sleep positional therapy to user 12. The vibratory, auditory, electric, magnetic, visual, somatosensory, and/or other sensory stimulation may include vibratory stimulation, auditory stimulation, visual stimulation, somatosensory stimulation, electrical stimulation, magnetic stimulation, a combination of different types of stimulation, and/or other stimulation. The vibratory, auditory, electric, magnetic, visual, somatosensory, and/or other sensory stimuli include vibrations, sounds, visual stimulation, somatosensory stimulation, haptic, electrical, magnetic, and/or other stimuli. The sensory stimulation may have an intensity, a timing, and/or other characteristics. For example, vibrations may be provided to user 12 to prompt user 12 to change posture, and/or take other actions. The vibrations may include one or more series of vibrations of a determined length separated from each other by an inter-vibration interval. The intensity, length, timing, and/or other characteristics of individual vibrations may be modulated. As another example, the sensory stimulation provided by sensory stimulator 16 may be provided via audio tones using bone conduction (e.g., through the teeth of user 12). The audio tones may have a volume, frequency, duration, inter tone interval, and/or other adjustable characteristics, for example. As yet another example, sensory stimulator 16 may be configured to provide audio playback through the bone conduction. The audio playback may comprise white noise, calming sounds, music, a wake-up alarm, sounds provided via wireless network (e.g., Bluetooth) connectivity, and/or other audio playback. In some embodiments, the audio playback may be caused by controller 18 (e.g., as described below) independent of the posture of user 12 and/or the sensory stimulation configured to prompt user 12 to change posture. These examples are not intended to be limiting.

Examples of sensory stimulator 16 may include one or more of a vibrator (e.g., with an oscillating transducer), a speaker, a coil generating a magnetic field, one or more light generators, and/or other devices. In some embodiments, sensory stimulator 16 is configured to adjust the type, intensity, timing, and/or other parameters of the stimulation provided to user 12. The adjustments may be responsive to entries and/or selections made by user 12 via electronic application 22, based on information from previous sleep sessions of user 12, based on an effectiveness of therapy provided to user 12, and/or responsive to or based on other information. Although sensory stimulator 16 is illustrated in FIG. 1 at a single location in system 10, this is not intended to be limiting. Sensory stimulator 16 may comprise stimulators disposed in a plurality of locations, such as for example, at various locations coupled to mandibular advancement mouthpiece 13, within housing 29, placed in an environment where user 12 sleeps (e.g., speakers and lighting devices in such a room), and/or at other locations. One or more separate stimulators 16 in these various locations may be in wired and/or wireless communication with controller 18 and/or other components of system 10, for example.

Controller 18 is configured to provide information processing capabilities in system 10. As such, controller 18 may comprise one or more of a digital processor, an analog processor, a digital circuit designed to process information, an analog circuit designed to process information, a state machine, and/or other mechanisms for electronically processing information. Although controller 18 is shown in FIG. 1 as a single entity, this is for illustrative purposes only. In some embodiments, controller 18 may comprise a plurality of processing units. These processing units may be physically located within the same device (e.g., within housing 29), or controller 18 may represent processing functionality of a plurality of devices operating in coordination. In some embodiments, a portion of controller 18 may be and/or be included in a computing device such as a desktop computer, a laptop computer, a smartphone, a tablet computer, a server, and/or other computing devices such as computing device 24 associated with user 12 and/or other people. Computing device 24 and/or other computing devices may run one or more electronic applications such as electronic application 22 having a graphical user interface configured to facilitate user interaction with system 10 (e.g., as described below).

Controller 18 is configured to determine whether the posture of user 12 breaches a posture threshold. Controller 18 is configured to make this posture threshold determination based on the output signals from posture sensor 14, and/or based on other information. In some embodiments, the posture threshold corresponds to a posture of user 12 that causes user 12 to experience sleep disordered breathing events such as snoring, apnea, and/or other sleep disordered breathing events. In some embodiments, the posture threshold corresponds to a supine position of user 12 and/or other body positions, for example. In some embodiments, controller 18 is configured to determine whether the posture of user 12 breaches a posture threshold responsive to one or more posture criteria (e.g., thresholds on accelerometer data in the output signals from sensor 14) that define the posture threshold being met (e.g., by either low-pass filter the information from an accelerometer, or using the information from the accelerometer and a gyroscope combinational to determine the orientation of system 10). Posture criteria are programmed at the manufacture of system 10, adjustable by user 12 and/or other users via user interface 25, electronic application 22, computing device 24, and/or other components of system 10, and/or determined in other ways.

Controller 18 is configured to cause sensory stimulator 16 to provide sensory stimulation to user 12 that is configured to prompt user 12 to change posture. The sensory stimulation configured to prompt user 12 to change posture is provided responsive to a determination that the posture of user 12 breaches the posture threshold. The sensory stimulation configured to prompt user 12 to change posture is provided to prompt user 12 to change posture (e.g., change head and/or neck position, roll over, etc.) so the posture of user 12 no longer breaches the posture threshold. The sensory stimulation configured to prompt user 12 to change posture may be, for example, vibrations, auditory stimulation (e.g., tones, music, etc.), and/or other stimulation. In some embodiments, the sensory stimulation configured to prompt user 12 to change posture may be programmed at the manufacture of system 10, may be adjustable by user 12 and/or other users, and/or may be determined in other ways. For example, in some embodiments, the sensory stimulation configured to prompt user 12 to change posture may be user customizable by type (e.g., vibrations, audio, or other types), intensity (e.g. mild, medium, strong), frequency, and/or other adjustable characteristics. These adjustments may be facilitated by controller 18 via user interface 25, electronic application 22, and/or other components of system 10. For example, in some embodiments, system 10 may be adjusted such that causing sensory stimulator 16 to provide the sensory stimulation that prompts user 12 to change posture comprises causing sensory stimulator 16 to provide a series of individual sensory stimuli (e.g., vibrations) that prompt user 12 to change posture.

In some embodiments, controller 18 is configured to determine whether user 12 experiences a sleep disordered breathing event. Controller 18 is configured to determine whether user 12 experiences a sleep disordered breathing event based on the information related to respiration of the user (e.g., in the output signals from posture sensor 14 and/or physiological sensor 20 as described above). For example, controller 18 may be configured such that any measure of tidal volume or airflow (generated from sound or movement sensors) over time may generate the necessary signal to determine the presence of sleep disordered breathing events, which are typically defined as a cessation or significant reduction in airflow over a greater than or equal to 10 s period. As another example, controller 18 may be configured such that an airflow measure along with accelerometer information can be used to detect the sleep-disordered breathing events, as well as the arousals that typically follow. As another example, actigraphy-only information may be used by controller 18 to detect sleep-disordered breathing events (e.g. number of arousals over time); or acoustic only (presence or absence of snoring) information can also be used by controller 18 to determine the presence of sleep disordered breathing. These examples are not intended to be limiting.

In some embodiments, controller 18 is configured to cause sensory stimulator 16 to cause delivery of the sensory stimulation responsive to a determination that user 12 is experiencing, and/or has experienced, one or more sleep disordered breathing events. For example, controller 18 may be configured to cause sensory stimulator 16 to deliver sensory stimulation to user 12 responsive to user 12 experiencing apnea or snoring (for example), whether the body (e.g., head) position of user 12 breaches the body position threshold. In some embodiments, controller 18 is configured to cause sensory stimulator 16 to deliver the sensory stimulation responsive to a determination that the posture of the user breached the posture threshold, and a determination that the user experienced a sleep disordered breathing event. For example, controller 18 may be configured to cause sensory stimulator 16 to provide the sensory stimulation responsive to user 12 being in a supine position and experiencing a sleep disordered breathing event such as an apnea or snoring. In such embodiments, controller 18 may not cause sensory stimulator to provide the sensory stimulation responsive to either condition (e.g., being in a supine position or experiencing a sleep disordered breathing event) by itself.

In some embodiments, controller 18 is configured to determine a sleep stage of user 12. Controller 18 is configured to determine a sleep stage of user 12 based on the information related to respiration of user 12 and/or other information. In some embodiments, controller 18 may be configured to determine the sleep stage of user 12 based on actigraphy, respiration patterns of user 12, and/or by other techniques. In some embodiments, actigraphy information, the respiration patterns, and/or other information may be indicative of brain activity in user 12 that indicates one or more of the sleep stages described above. In some embodiments, controller 18 is configured to cause sensory stimulator 16 to provide the sensory stimulation to user 12 responsive to user 12 experiencing an arousal, and/or being in a wakeful or light stage (e.g., REM and/or N1) of sleep.

In some embodiments, controller 18 (and/or sensor 14 and/or 20) is configured to allow user 12 to fall asleep in a supine position (and/or another head or body posture that would normally breach the body posture threshold) and begin causing sensory stimulator 16 to provide the sensory stimulation to user 12 after a predetermined period of time elapses after user 12 begins to try to fall asleep, after a transition from wakefulness to sleep (e.g., a REM, N1, or another sleep stage) is detected, and/or responsive to other conditions. For example, controller 18 may be configured to ignore information in the sensor 14 and/or 20 output signals during the predetermined period of time, sensors 14 and/or 20 may be configured to not generate output signals, and/or not provide information related to body posture in the output signals during the predetermined period of time, controller 18 may receive the information in the output signals but not determine body posture of user 12 during the predetermined period of time, and/or other operations may be performed. In some embodiments, delaying the sensory stimulation is configured to help user 12 fall asleep, for example. In some embodiments, the predetermined period of time is determined at manufacture of system 10, adjustable by user 12 and/or others (e.g., via user interface 25, electronic application 22, etc.), determined by controller 18 based on the information in the output signals from sensors 14 and/or 20, determined based on information from previous sleep sessions of user 12, and/or based on other information.

Electronic Application 22 is executed by computing device 24 associated with user 12. Electronic application 22 is in communication with controller 18, posture sensor 14, physiological sensor 20, sensory stimulator 16, electronic storage 26, user interface 25, communications components 31, and/or other components of system 10. In some embodiments, electronic application 22 is configured to facilitate review of generated and/or stored information related to sleep of user 12, respiration of user 12, stimulation provided to user 12, and/or other information. In some embodiments, the information related to sleep of user 12, respiration of user 12, simulation provided to user 12, and/or other information comprises information related to: a quantity, frequency, timing, and/or type of sleep disordered breathing events in the user; a sleep stage of the user; an effectiveness of the mandibular advancement mouthpiece; a recommended mandibular advancement mouthpiece adjustment; the sensory stimulation provided to the user, and/or other information. In some embodiments, this information is determined by controller 18, electronic application 22, and/ or other components of system 10. In these embodiments, controller 18 may be configured to monitor and generate (e.g., based on the information in the output signals from sensor 14, sensor 20, and/or other information) user information related to usage and efficacy of mandibular mouthpiece 13 (e.g., determining and/or recording a number of sleep disordered breathing events in user 12, and/or other information based on the output signals). For example, if there is an absence of and/or decrease in (e.g., relative to prior sleep sessions and/or relative to when mandibular advancement mouthpiece 13 was previously adjusted) sleep disordered breathing events, controller 18 and/or electronic application 22 may determine that the advancement of mandibular advancement mouthpiece 13 is effective. Conversely, if sleep disordered breathing events occur, and/or if there is an increase in sleep disordered breathing events relative to prior sleep sessions (and/or when mandibular advancement mouthpiece 13 was previously adjusted), controller 18 and/or electronic application 22 may determine that the advancement of mandibular advancement mouthpiece 13 is ineffective. Controller 18 and/or electronic application 22 may be configured such that electronic application 22 then displays a message to user 12 that the advancement of the lower jaw needs to be increased (or otherwise adjusted). As another example, controller 18 and/ or electronic application 22 may monitor and generate user information comprising an apnea hypopnea index (AHI), a number of instances of providing vibrations and/or other sensory stimulation, a percent of the sleep session spent in a supine position (e.g., in a position that breaches the posture threshold), etc.

In these embodiments, controller 18 and/or electronic application 22 may be configured to generate longitudinal (diary) data that may be recalled (e.g., from electronic storage 26) and reviewed (e.g., using electronic application 22) by user 12 and/or others. In these embodiments, electronic application 22 and/or controller 18 may be configured such that the user information related to usage and efficacy and/or other user information may be wirelessly transferrable to or from a computing device such as computing device 24 and/or other computing devices.

Computing device 24 may be associated with user 12 and/or other people. Computing device 24 may be a desktop computer, a laptop computer, a smart phone, a tablet, or any other networked computing device having a display, a user input device (e.g., buttons, keys, voice recognition, or a single or multi-touch touchscreen), memory (such as a tangible, machine-readable, non-transitory memory), a network interface, an energy source (e.g., a battery), and a processor coupled to these components. The memory of mobile computing device 24 may store instructions that when executed by the associated processor provide an operating system and various applications, including electronic application 22. In some embodiments, electronic application 22 is operative to provide a graphical user interface that communicates with other components of system 10 (e.g., communications components 31, controller 18, etc.) and facilitates user interaction with system 10.

User interface 25 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of sensor 14, sensor 20, sensory stimulator 16, controller 18, electronic application 22, computing device 24, electronic storage 26, power supply 28, communications components 31, and/or other components of system 10. In some embodiments, some or all of user interface 25 may be and/or be included in a computing device such as computing device 24 (e.g., a desktop computer, a laptop computer, a smartphone, a tablet computer, and/or other computing devices.

Examples of interface devices suitable for inclusion in user interface 25 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 25 comprises a plurality of separate interfaces. In some embodiments, user interface 25 comprises at least one interface that is provided integrally with housing 29, integrally with computing device 24, and/or other components of system 10. In some embodiments, user interface 25 is configured to communicate wirelessly with communications components 31, controller 18, and/or other components of system 10.

It is to be understood that other communication techniques, either hard-wired or wireless, are also contemplated by the present disclosure as user interface 25. For example, the present disclosure contemplates that user interface 25 may be integrated with a removable storage interface provided by electronic storage 26. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 25 comprise, but are not limited to, an RS-232 port, RF link, an IR link, modem (telephone, cable or other). In short, any technique for communicating information with system 10 is contemplated by the present disclosure as user interface 25.

Electronic storage 26 comprises electronic storage media that electronically stores information. The electronic storage media of electronic storage 26 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 26 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 26 may store software algorithms, information determined by controller 18, information received via user interface 25 and/or sensors 14 and 20, and/or other information that enables system 10 to function as described herein. Electronic storage 26 may be (in whole or in part) a separate component within system 10, or electronic storage 26 may be provided (in whole or in part) integrally with one or more other components of system 10 (e.g., within housing 29).

Power supply 28 is configured to power posture sensor 14, physiological sensor 20, sensory stimulator 16, controller 18, user interface 25, electronic storage 26, communications components 31, and/or other components of system 10 in a portable manner. Power supply 28 may comprise one or more power sources connected in series and/or in parallel. In some embodiments, power supply 28 is rechargeable. Power supply 28 may be recharged via a home AC power source, a car battery outlet, an airplane power outlet, a USB port, a non-contact charging circuit, and/or other recharging methods. In some embodiments, power supply 28 may comprise a rechargeable battery that is inductively charged. In some embodiments, the inductive charger for power supply 28 may also function as an Ultra Violet (UV) cleaner for mandibular advancement mouthpiece 13. Examples of portable power sources that may be included as power supply 28 include one or more DC batteries, Lithium Ion and/or Lithium Polymer Cells, Nickel Metal Hydride, and/or other portable power sources.

Communications components 31 comprise components that facilitate communication of information via a network (e.g., the internet), equipment related to Wi-Fi technology, equipment related to Bluetooth® technology, input/output interfaces, and/or other resources. Communications components 31 may be configured to communicate with electronic application 22, computing device 24, and/or other components of system 10 via wired and/or wireless connections, via a network (e.g., a local area network and/or the internet), via cellular technology, via Wi-Fi technology, and/or via other resources. In some embodiments, communications components 31 may be configured to communicate via a text message, an email, a phone call, an electronic app and/or web page (e.g., electronic application 22, a web page displayed by computing device 24, etc.), an electronic app notification, and/or with other communications.

Housing 29 is configured to contain or otherwise house posture sensor 14, physiological sensor 20, sensory stimulator 16, controller 18, user interface 25, electronic storage 26, power supply 28, communications components 31, and/or other components of system 10. Housing 29 is configured to contain the components of system 10 in a space small enough to be comfortably coupled to mandibular advancement mouthpiece 13 when mouthpiece 13 is worn by user 12 during a sleep session. In FIG. 1, posture sensor 14, physiological sensor 20, sensory stimulator 16, controller 18, user interface 25, electronic storage 26, power supply 28, communications components 31, and/or other components of system 10 are shown housed by housing 26 and forming a single entity. This is not intended to be limiting. Some and/or all of the components of system 10 and/or other components may form one or more separate devices. For example, posture sensor 14, physiological sensor 20, and/or other components of system 10 may be separately coupled to mandibular advancement mouthpiece 13, outside of housing 29. As another example, sensory stimulator 16 may be or include speakers configured to direct auditory stimulation toward user 12. The speakers may be placed in the environment where user 12 sleeps, separate from housing 29, for example. These devices may be configured to communicate wireless and/or via wires with other components of system 10 and/or other devices.

Figure 3:
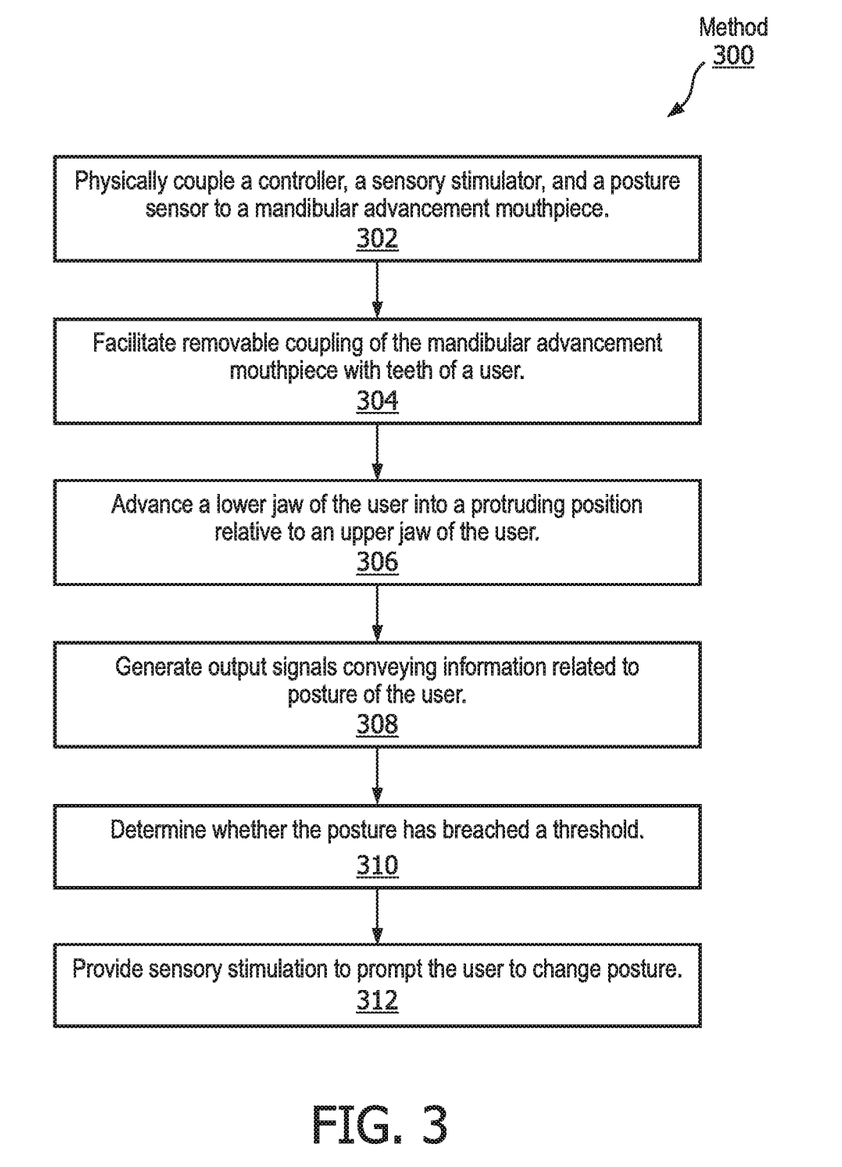
FIG. 3 illustrates a method for providing mandibular advancement and sleep positional therapy to a user for a sleep session, in accordance with one or more embodiments.

FIG. 3 illustrates method 300 for providing mandibular advancement and sleep positional therapy to a user for a sleep session with a therapy system. The system comprises one or more posture sensors, one or more physiological sensors, one or more sensory stimulators, one or more controllers, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, at least some of method 300 may be implemented in one or more processing devices such as one or more controllers 18 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

Operation 302 comprises facilitating physically coupling the controller, the one or more sensory stimulators, the one or more posture sensors, the one or more physiological sensors, and/or other components to the mandibular advancement mouthpiece. The controller, the one or more sensory stimulators, the one or more posture sensors, the one or more physiological sensors, and/or other components are physically coupled to the mandibular advancement mouthpiece (1) via a housing that protrudes from the mandibular advancement mouthpiece outside a mouth of the user, (2) along an interior lower jaw surface of the mandibular advancement mouthpiece; and/or (3) between upper and lower jaw portions of the mandibular advancement mouthpiece. In some embodiments, the physical coupling between the controller, the one or more sensory stimulators, the one or more sensors, and the mandibular advancement mouthpiece is releasable. In some embodiments, operation 302 is performed by a controller, one or more sensory stimulators, one or more posture sensors, one or more physiological sensors, and a mandibular advancement mouthpiece the same as or similar to controller 18, sensory stimulator 16, posture sensor 14, physiological sensor 20, and a mandibular advancement mouthpiece (shown in FIG. 1 and described herein).

Operation 304 comprises facilitating removable coupling of the mandibular advancement mouthpiece with teeth of the user. In some embodiments, a shape and/or form factor of the mandibular advancement mouthpiece may be configured to engage a corresponding shape and/or form factor of the teeth of the user. In some embodiments, operation 304 is performed by a mandibular advancement mouthpiece the same as or similar to mandibular advancement mouthpiece 13 (shown in FIG. 1 and described herein).

At an operation 306, the lower jaw of the user is advanced into a protruding position relative to an upper jaw of the user to increase a size of an airway of the user. In some embodiments, operation 306 comprises adjusting or fixing an amount the lower jaw of the user advances into the protruding position. In some embodiments, operation 306 is performed by a mandibular advancement mouthpiece the same as or similar to mandibular advancement mouthpiece 13 (shown in FIG. 1 and described herein).

At an operation 308, output signals conveying information related to the posture of a user are generated. The output signals are generated during a sleep session of the user and/or at other times. In some embodiments, operation 308 is performed by one or more sensors the same as or similar to posture sensor 14 (shown in FIG. 1 and described herein).

At an operation 310, a determination of whether the posture of the user breaches a posture threshold is made. In some embodiments, the posture threshold indicates whether the user is in a supine position. The posture determination is made based on the information in the output signals from the one or more posture sensors and/or based on other information. In some embodiments, operation 310 is performed by a controller the same as or similar to controller 18 (shown in FIG. 1 and described herein).

At an operation 312, sensory stimulation configured to prompt the user to change posture is provided to the user. The sensory stimulation configured to prompt the user to change posture is provided responsive to a determination that the posture of the user breaches the posture threshold. The sensory stimulation configured to prompt the user to change posture is provided to prompt the user to change posture, so the posture of the user no longer breaches the posture threshold. In some embodiments, operation 312 is performed by a sensory stimulator the same as or similar to sensory stimulator 16 (shown in FIG. 1 and described herein).

In some embodiments, operations 308-312 comprise generating output signals conveying information related to respiration of the user (e.g., with the one or more posture sensors and/or the one or more physiological sensors), determining whether the user experiences a sleep disordered breathing event based on the information related to respiration of the user, and causing the one or more sensory stimulators to deliver the sensory stimulation based on a determination that the user experienced a sleep disordered breathing event. In some embodiments, operations 308-312 comprise generating output signals conveying information related to respiration of the user, determining whether the user experiences a sleep disordered breathing event based on the information related to respiration of the user, and causing the one or more sensory stimulators to deliver the sensory stimulation responsive to: a determination that the posture of the user breached the posture threshold, and a determination that the user experienced a sleep disordered breathing event. In some embodiments, the one or more physiological sensors comprise a microphone, for example.

In some embodiments, operations 308-312 comprise generating, with the one or more posture sensors and/or the one or more physiological sensors, output signals conveying information related to respiration of the user, determining a sleep stage of the user based on the information in the output signals, and causing, with the controller via the one or more sensory stimulators, delivery of the sensory stimulation based on the sleep stage of the user. For example, method 300 may comprise causing the one or more sensory stimulators to provide the sensory stimulation to the user responsive to the user experiencing an arousal, and/or being in a wakeful or light stage of sleep.

In some embodiments, the system further comprises an electronic application executed by a computing device associated with the user. In such embodiments, method 300 further comprises (operation not illustrated in FIG. 3) facilitating review of information related to sleep of the user, respiration of the user, and/or other information. The information related to sleep of the user and/or respiration of the user (e.g., determined by the controller and/or the electronic application) comprises information related to: a quantity, frequency, timing, and/or type of sleep disordered breathing events in the user; a sleep stage of the user; an effectiveness of the mandibular advancement mouthpiece; a recommended mandibular advancement mouthpiece adjustment; the sensory stimulation provided to the user; and/or other information. In some embodiments, this operation is performed by a controller and an electronic application the same as or similar to controller 18 and electronic application 22 (shown in FIG. 1 and described herein).

In the claims, any reference signs placed between parentheses shall not be construed as limiting the claim. The word "comprising" or "including" does not exclude the presence of elements or steps other than those listed in a claim. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide mandibular advancement and sleep positional therapy to a user for a sleep session, the system comprising:
   a mandibular advancement mouthpiece configured to:
   removably couple with teeth of the user; and
   advance a lower jaw of the user into a protruding position relative to an upper jaw of the user to increase a size of an airway of the user;
   one or more posture sensors fixedly coupled to the mandibular advancement mouthpiece and configured to generate output signals conveying information related to a posture of the user;
   one or more sensory stimulators fixedly coupled to the mandibular mouthpiece and configured to provide sensory stimulation to the user; and
   a controller fixedly coupled to the mandibular advancement mouthpiece and electronically coupled to the one or more posture sensors and the one or more sensory stimulators, the controller configured to:
   determine, based on the output signals, whether the posture of the user has breached a posture threshold, and, responsive to a breach, cause the one or more sensory stimulators to provide first sensory stimulation to the user to prompt the user to change posture such that the posture of the user no longer breaches the posture threshold;
   and
   wherein the controller, the one or more sensory stimulators, and the one or more posture sensors are fixedly coupled to the mandibular advancement mouthpiece:
   (1) via housing that protrudes from the mandibular advancement mouthpiece outside a mouth of the user when the mandibular advancement mouthpiece is positioned in the mouth of the user,
   (2) along an interior lower jaw surface of the mandibular advancement mouthpiece so as to be disposed within the mouth of the user when the mandibular advancement mouthpiece is positioned in the mouth of the user; and/or
   (3) between upper and lower jaw portions of the mandibular advancement mouthpiece so as to be disposed within the mouth of the user when the mandibular advancement mouthpiece is positioned in the mouth of the user.

2. The system of claim 1, wherein a physical coupling between the controller, the one or more sensory stimulators, the one or more posture sensors, and the mandibular advancement mouthpiece is releasable.

3. The system of claim 1, wherein the one or more posture sensors comprise an accelerometer.

4. The system of claim 3, wherein the accelerometer is configured to generate output signals conveying information related to respiration of the user, and
   wherein the controller is further configured to determine whether the user experiences a sleep disordered breathing event based on the information related to respiration of the user.

5. The system of claim 4, wherein the controller is further configured to cause the one or more sensory stimulators to deliver the sensory stimulation responsive to:
   a determination that the posture of the user breached the posture threshold, and
   a determination that the user experienced a sleep disordered breathing event.

6. The system of claim 3, wherein the accelerometer is configured to generate output signals conveying information related to respiration of the user,
   wherein the controller is further configured to determine a sleep stage of the user based on the information related to respiration of the user; and
   wherein the controller is further configured to cause the one or more sensory stimulators to provide the sensory stimulation to the user responsive to the user experiencing an arousal, and/or being in a wakeful or light stage of sleep.

7. The system of claim 1, further comprising one or more physiological sensors configured to generate output signals conveying information related to respiration of the user,
   wherein the controller is configured to determine whether the user experiences a sleep disordered breathing event and/or a sleep stage of the user based on the information in the output signals from the one or more physiological sensors, and
   wherein the controller is further configured to cause delivery of the sensory stimulation based on the determination of whether the user experienced a sleep disordered breathing event and/or the sleep stage of the user.

8. The system of claim 7, wherein the one or more physiological sensors comprise a microphone.

9. The system of claim 1, wherein the mandibular advancement mouthpiece is configured such that an amount the lower jaw of the user advances into the protruding position is adjustable or fixed.

10. The system of claim 1, further comprising an electronic application executed by a computing device associated with the user, the electronic application in communication with the controller, the one or more posture sensors, and/or the one or more sensory stimulators, the electronic application configured to facilitate review of information related to the sleep of the user, and/or the respiration of the user, the information related to the sleep of the user and/or the respiration of the user comprising information related to:
    a quantity, frequency, timing, and/or type of sleep disordered breathing events in the user;
    a sleep stage of the user;
    an effectiveness of the mandibular advancement mouthpiece;
    a recommended mandibular advancement mouthpiece adjustment; and/or
    the sensory stimulation provided to the user.

11. The system of claim 10, wherein the controller is further configured to determine the information related to the sleep of the user, and/or the respiration of the user.

* * * * *